(12) United States Patent
Farronato (10) Patent No.: US 11,890,148 B2
(45) Date of Patent: Feb. 6, 2024

(54) SYSTEM AND METHOD FOR DYNAMIC AUGMENTED REALITY IMAGING OF AN ANTOMICAL SITE

(71) Applicant: Marco Farronato, Milan (IT)

(72) Inventor: Marco Farronato, Milan (IT)

(*) Notice: Subject to any disclaimer, the term of this patent is extended or adjusted under 35 U.S.C. 154(b) by 0 days.

(21) Appl. No.: 17/290,998

(22) PCT Filed: Dec. 13, 2019

(86) PCT No.: PCT/IB2019/060760
§ 371 (c)(1),
(2) Date: May 4, 2021

(87) PCT Pub. No.: WO2020/121270
PCT Pub. Date: Jun. 18, 2020

(65) Prior Publication Data
US 2022/0031421 A1    Feb. 3, 2022

(30) Foreign Application Priority Data
Dec. 14, 2018 (IT) .......................... 102018000011117

(51) Int. Cl.
*A61B 90/00* (2016.01)
*A61B 34/20* (2016.01)
(Continued)

(52) U.S. Cl.
CPC ............ *A61B 90/361* (2016.02); *A61B 34/10* (2016.02); *A61B 34/20* (2016.02); *G06T 19/006* (2013.01);
(Continued)

(58) Field of Classification Search
CPC . A61B 90/361; A61B 2090/365; A61B 34/20; A61B 34/10; G06T 19/006
(Continued)

(56) References Cited

U.S. PATENT DOCUMENTS

| 11,219,428 B2* | 1/2022 | Burkholz ......... A61B 5/150793 |
| 2012/0182294 A1* | 7/2012 | Cordon Garcia ....... G06T 17/00 |
| | | 345/419 |

(Continued)

FOREIGN PATENT DOCUMENTS

EP    3138526 A1    3/2017

*Primary Examiner* — Javid A Amini
(74) *Attorney, Agent, or Firm* — Carmel Patent Agency; Robert J. Ballarini (57) ABSTRACT

A system for dynamic augmented reality imaging of an anatomical site includes at least one image capturing device for capturing first real-time images of the site, at least one display device for displaying first images captured by the device, storage means for storing at least one second anatomical image of the site and an electronic device having a controller configured to receive and process the images. The controller is configured to display an augmented reality image obtained by superimposing images on the first image by identifying common reference elements of the images, and the common reference elements are identified automatically or manually. The second image is in 3D made up of portions of fan or cone beam computed tomography or magnetic resonance images depicting internal structures of the site. The augmented reality image is clipped to the site by the elements, irrespective of the spatial position of the electronic device.

15 Claims, 3 Drawing Sheets

(51) Int. Cl.
*G06T 19/00* (2011.01)
*A61B 34/10* (2016.01)

(52) U.S. Cl.
CPC ... *A61B 2034/104* (2016.02); *A61B 2034/107* (2016.02); *A61B 2034/2048* (2016.02); *A61B 2090/365* (2016.02); *A61B 2090/372* (2016.02); *G06T 2210/41* (2013.01)

(58) Field of Classification Search
USPC .......................................................... 345/419
See application file for complete search history.

(56) References Cited

U.S. PATENT DOCUMENTS

| | | | |
|---|---|---|---|
| 2016/0220105 A1* | 8/2016 | Duret ................. | A61B 1/00048 |
| 2016/0346047 A1* | 12/2016 | Tripathi ................. | A61B 90/37 |
| 2017/0007350 A1* | 1/2017 | Popovic ................. | A61B 34/10 |
| 2017/0065379 A1* | 3/2017 | Cowburn ............ | A61C 13/0004 |
| 2018/0168781 A1* | 6/2018 | Kopelman ....... | A61B 1/000094 |

* cited by examiner

SYSTEM AND METHOD FOR DYNAMIC AUGMENTED REALITY IMAGING OF AN ANTOMICAL SITE

TECHNICAL FIELD

The present invention generally finds application in the field of controller-assisted dentistry, namely in the field of medicine, orthodontics, dental surgery and/or diagnosis, and particularly relates to a system for augmented reality imaging of an anatomical site.

According to a further aspect, the invention relates to a method of dynamic augmented reality imaging of an anatomical site using such system.

BACKGROUND ART

Iatrogenic errors are known to be often caused by a lack of coordination between diagnostic data and the anatomical site, due to the risk of collision with critical and non-critical structures e.g. vascular, nervous, lymphatic or other complex structures.

In addition, 3D diagnostic imaging is a basic medical procedure prescribed for patients having particular problems or surgical difficulties, but also for certain routine operations requiring its use.

Generally, this kind of diagnostic procedure is carried out through Cone Beam Computed Tomography (CBCT), Multiple Detector Computed Tomography (MDCT), Nuclear Magnetic Resonance (NMR) and intraoral scanning, with images having incomplete information, and later non-objective interpretation by a healthcare professional.

The information obtained from diagnostic imaging are also known to be recorded in a standard .dcm format and to be only able to be displayed by electronic devices with dedicated applications installed thereon.

A further drawback of these known solutions is that, while this type of images constitutes a three-dimensional reconstruction of two-dimensional data, they can only be displayed on flat screens and cannot be accurately superimposed on the patient before or during medical procedures or through dynamic procedures.

Another drawback of such solutions is that transfer of digital data to the surgical field in digitally planned and executed procedures requires the use of systems that use 3D printing or digitally assisted procedures with infrared devices using reference markers.

An additional drawback of these known solutions is that the interpretation of diagnostic images is closely related to the expertise and skills of the healthcare professional, which prevents the patient from having a high perception of treatment effectiveness.

In view of at least partially obviating these drawbacks, systems have been developed for Augmented Reality imaging of an anatomical site through the deployment of applications of various kinds.

EP3138526 discloses an imaging system comprising an image capturing device for capturing first real-time images of an anatomical site and at least one biometric sensor for obtaining biometric data from a patient.

In addition, the system comprises a controller having a memory configured to store a plurality of second anatomical images of the relevant site and adapted to process the first and second images and biometric data to generate an augmented reality image.

Then, this augmented reality image is later projected onto the anatomical site by a display device for simultaneous display of the second images and/or the biometric data during the surgical operations that can be done by a healthcare professional on the anatomic site.

A first drawback of this known solution is that the capture and display devices are distinct and separate element, which increases manufacturing costs.

A further drawback of this solution is that the system is limited to a narrow range of surgery and requires the use of devices such as high definition cameras, projection devices and high-technology dedicated applications.

Another drawback is that the capture and display devices do not comprise instruments adapted to determine their position relative to the anatomic site.

Therefore, the capture and/or display devices must be calibrated or repositioned as the type of the anatomical site or the instruments required for the activities that are carried out by the healthcare professional change.

A further drawback is that efficient operation requires the anatomical site to be stable and motionless, which prevents the system from being used for any procedure.

Technical Problem

In view of the prior art, the technical problem addressed by the present invention consists in providing a system and a method for augmented reality imaging of an anatomical site that is simple and inexpensive and can assist the healthcare professional during surgery and diagnosis, irrespective of the position of the anatomical site.

DISCLOSURE OF THE INVENTION

The object of the present invention is to obviate the above drawbacks, by providing a system and a method for dynamic augmented reality imaging of an anatomical site, that is highly efficient and relatively cost-effective.

A particular object of the present invention is to provide a system of the aforementioned type that can assist the healthcare professional during the diagnosis and/or intra-surgery steps, irrespective of the position and/or movements of the anatomical site.

A further object of the present invention is to provide a method of the aforementioned type that has a reduced number of steps.

Another object of the present invention is to provide a system of the aforementioned type that can reduce the overall surgical times by the healthcare professional.

A further object of the present invention is to provide a system and a method of the aforementioned type that can be used in a simple manner, independent of the skills of the healthcare professional.

Another object of the present invention is to provide a system of the aforementioned type that allows quick and accurate superimposition of first real-time images and second anatomical images.

A further object of the present invention is to provide a system of the aforementioned type that can be remotely controlled, manually or with the help of artificial intelligence to provide instant feedback to the healthcare professional.

Yet another object of this invention is to provide a system that has very low manufacturing costs.

A further object of the present invention is to provide a system of the aforementioned type that can provide and display previously planned information to support the actions that can be performed by the healthcare professional.

Another object of the present invention is to provide a system of the aforementioned type that affords movement of the healthcare professional or the anatomical site without requiring any further calibration.

These and other objects, as more clearly explained hereinafter, are fulfilled by a system for dynamic augmented reality imaging of an anatomical site, which comprises at least one image capturing device for capturing first real-time images of the anatomical site, at least one display device for real-time display of the first images captured by the capture device, storage means for storing at least one second anatomic image of the site and an electronic device comprising a controller which is configured to receive and process the first and second images.

The controller is configured to have the display image to display an augmented reality image obtained by superimposing the second image on the first image by identifying the common reference elements of the first and second images, the common reference elements being identified automatically by the controller or manually by a healthcare professional.

According to a peculiar aspect of the invention, the second image is a 3D image and is formed by portions of fan beam or cone beam computed tomography (CBCT) or magnetic resonance images depicting internal structures of the anatomical site that are invisible to the naked eye and the augmented reality image is clipped to the anatomical site by means of the reference elements, irrespective of the spatial position of the electronic device during the displacements of the latter relative to the anatomical site (C).

In particular, the second images may be possibly superimposed on additional images obtained by scanning hard tissues, e.g. by intraoral scanning in the field of dentistry or photogrammetry.

According to a further aspect, the invention relates to a method of augmented reality imaging of an anatomical site using such system.

Advantageous embodiments of the invention are obtained in accordance with the dependent claims.

BRIEF DESCRIPTION OF THE DRAWINGS

Further features and advantages of the invention will be more apparent from the detailed description of a preferred, non-exclusive embodiment of a system for augmented reality imaging of an anatomical site and the relevant imaging method, which are described as a non-limiting example with the help of the annexed drawings, in which:

FIGS. 3A to 6 are schematic views of the system of FIG. 2 in different operating steps;

DETAILED DESCRIPTION OF A PREFERRED EXEMPLARY EMBODIMENT

Particularly referring to the figures, there is shown a system for augmented reality imaging of an anatomical site C, generally designated by numeral 1.

As used herein, the term "anatomical site" is intended to designate a portion of the body of a patient undergoing non-invasive diagnosis, pre-surgery, inter-surgery and/or post-surgery or follow-up and that is internally invisible to the naked eye.

The system 1 comprises at least one image capturing device 2 for capturing first real-time images 3 of the anatomical site C and at least one display device 4 for displaying the first images 3 captured by the capture device 2 in real time.

Figure 2:
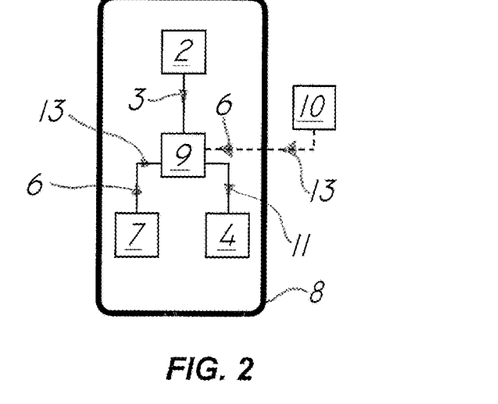

As shown in FIG. 2, the system 1 comprises storage means 7 for storing at least one second anatomical image 6 of the anatomical site C.

Storage means 7 for storing the second anatomical images 6 of the anatomical site C and an electronic device 8 having a controller 9 configured to receive and process the first 3 and the second images 6 are also provided.

As used herein, the term "controller" is intended to designate an electronic component which is powered by a power source and has a microprocessor unit, a plurality of peripheral control and/or communication devices for promoting the execution of a computer application.

As is known, the storage means 7 may be of non-volatile solid-state flash memory type, that can maintain the stored information even when they are not connected to power source.

Preferably, the storage means 7 may be incorporated in the electronic device 8 or in an external server 10, or on-line in a cloud, that can connect via wireless means to the electronic device 8 at high speed (4g, 5g) as schematically shown in FIG. 2.

In a preferred embodiment of the invention as shown in the figures, the electronic device 8 comprises an accelerometer and a gyroscope and the capture device 2 and the display device 4 may be incorporated in the electronic device 8.

For this purpose, the electronic device 8 may be a smartphone or a tablet, wherein the capture device 2 for capturing the first images 3 consists of a camera and the display device 4 consists of a touchscreen of the device 8.

In an exemplary, non-limiting embodiment of the invention, the electronic device 8 may comprise a smartphone whose operating system is either iOS 10.1 or later, or Android Nuogat version 7.0 or later.

The controller 9 is configured to have the display device 4 display an augmented reality image 11 obtained by superimposing the second image 6 on the first image 3 with common reference elements 12 being identified in the first image 3 and the second image 6.

Figure 4:
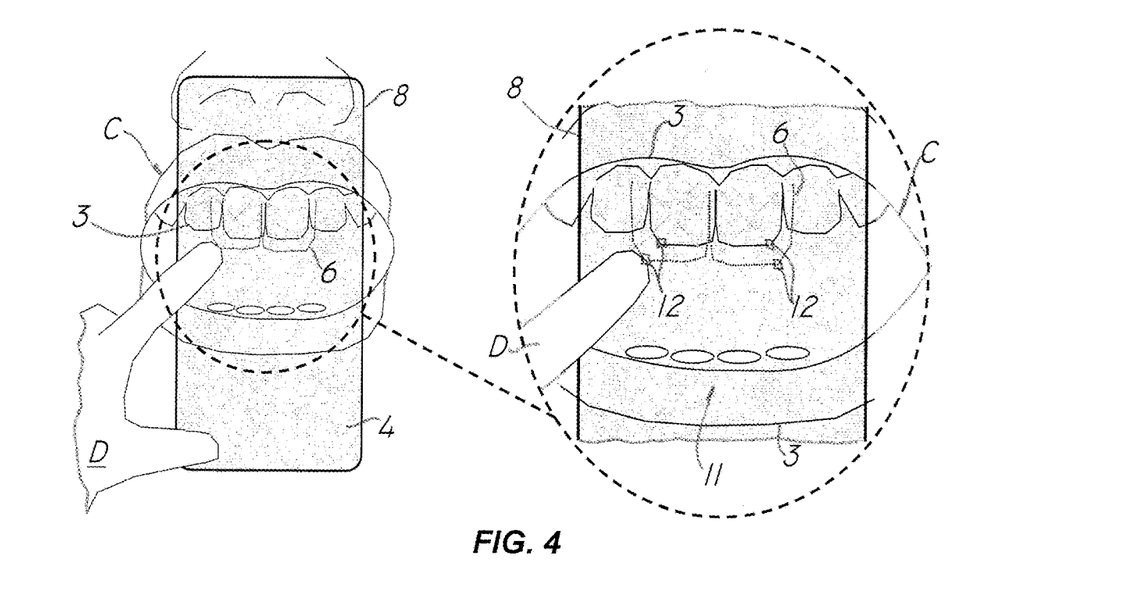

As shown in FIG. 4, the reference elements 12 are identified automatically by the controller 9 or manually by a healthcare professional D.

According to a peculiar aspect of the invention, the second images are 3D images and are obtained from portions of fan beam or cone beam computed tomography (CBCT) or magnetic resonance images showing internal structures of the anatomical site C that are invisible to the naked eye and the augmented reality image 11 is clipped to the anatomical site C by means of the common reference elements 12, irrespective of the spatial position of the electronic device 8 during the displacements of the latter relative to the anatomical site C.

In particular, the portions of fan beam or cone beam computed tomography or magnetic resonance images may be obtained using by suitable equipment on the anatomical site C during diagnosis or pre-surgery.

Furthermore, the second images 6 may be possibly superimposed on additional second images obtained by scanning hard tissues, e.g. by photogrammetry or intraoral scanning in the field of dentistry.

It will be appreciated that the system 1 of the invention allows accurate superimposition of the second anatomical images 6 and the first real-time images 3 of the anatomical site C both during diagnosis and/or pre-surgery and during inter-surgery procedures, carried out by the healthcare professional D.

Thus, the healthcare professional D may interact with the anatomical site C and observe the latter via the electronic device 8 which depicts the first real-time images 3 superimposed on the second images 6 captured beforehand, thereby being able to observe the anatomical site C in its entirety.

In other words, the augmented reality image 11 is stabilized in space using the common reference elements 12, while tracking the movements of the anatomical site C along the three axes in space (roto-translation, inclination, laterality) and enhancing perception by the healthcare professional D allowing him to watch in real time elements of the anatomical site C that are visible and non-visible to the naked eye as if the tissues were transparent.

As used herein, the term "augmented reality image" is intended to designate an image obtained by superimposition of one or more virtual images, not visible to the naked eye on real images, visible to the naked eye in order to enhance visual perception by the healthcare professional.

In the preferred embodiment of the invention, the anatomical site C may comprise the stomatognathic system, the common reference elements 12 may correspond to elements of the image of the dental structure or other anatomical structures and preferably central incisors.

In this embodiment, the common reference points 12 required for superimposition of the first 3 and the second images 6 may be manually selected by the healthcare professional D with the help of lip retractors.

Figure 3A:
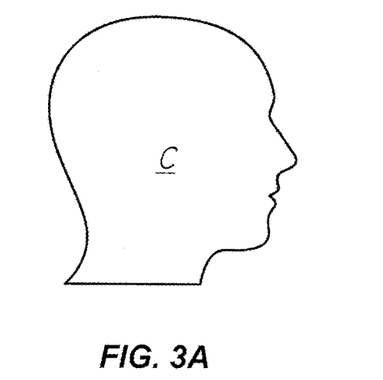
Figure 3B:
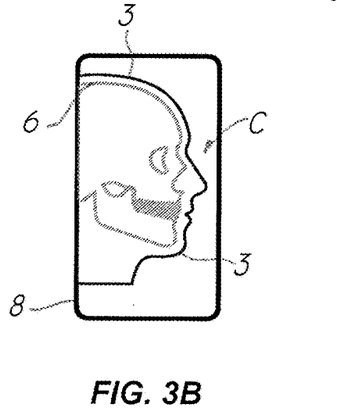
Figure 3C:
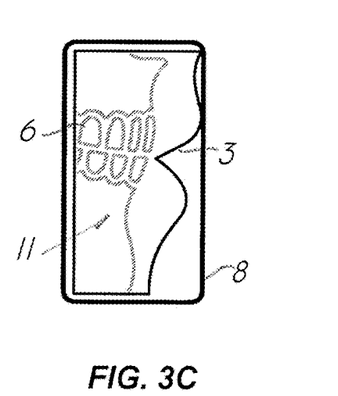

By way of example and without limitation, the second Images 6 may be magnetic resonance images of the dental system of the patient or images depicting critical structures of vascular, nervous, lymphatic or other type such as complex radical systems of other teeth and hence internal structures in the anatomical site C, invisible to the naked eye, as shown in FIGS. 3A to 3C.

Alternatively, the common reference elements 12 may comprise the left and right infra-orbital points, the lowest outlet of the infraorbital canal, the right and left parts of the nasion, anthropometric or cephalometric points or relevant points of craniofacial structures.

In this embodiment, the first images 3 may correspond to real-time images of the mouth of the patient, visible to the naked eye both the healthcare professional D and by the capture device 2, whereas the second images 6 may correspond to 3D X-ray reports or images showing anatomical structures that are not visible to the naked eye by the healthcare professional D or are not visible from the first images 3.

Then, the controller 9 may detect the common reference elements 12 from the first images 3 of the patient that have been captured by the capture device 2 and from the second anatomical images 6 of the same patient, using Artificial Intelligence algorithms or by the healthcare professional D using a cursor or moving his/her fingers on the display device 4 if the latter consists of a touchscreen.

Then the controller 9 may superimpose images 3, 6 and allow simultaneous display thereof on the display device 4 through the Augmented Reality image 11 which will be of dynamic three-dimensional type, i.e. able to move according to the movements of the mouth or head of the patient and/or according to the movement of the electronic device 8 relative to the anatomical site C.

Possibly, the electronic device 8 may have infrared light for real-time tracking of surfaces, or echo sounds or magnetic fields to increase its accuracy in obtaining the first images 3 or of the common reference elements 12.

In an exemplary non-limiting embodiment of the invention, the electronic device 8 may comprise a controller 9 having an application installed thereon, which is developed on frameworks selected from the group comprising ARkit Ulkit, with the programming language SWIFT+C and with libraries selected from the group comprising foundation, c.lib, stdio pipes.h, metal and imebra.

As is known, the second images 6 may be stored as .dcm in the storage means 7 and may comprise a plurality of information units classified as Hounsfield Units (HU) and related to a gray scale corresponding to the density of the elements being imaged. The plurality of information units may also relate to the 3D space positions of the items being imaged.

If they are obtained from an intraoral scanner, the second images 6 may also be stored in the STL format and have no HU information, without departure from the scope of the present invention.

In addition, the display device 4 of the electronic device 8 may provide magnification of the augmented reality image 11 by increasing the size of the first 3 and the second images 6 without releasing them from the common reference elements 12.

Therefore, in the preferred embodiment of the invention, in which the electronic device 8 consists of a smartphone, this magnification may be obtaining by the healthcare professional D moving his/her fingers on the touchscreen display device 4, as best shown in FIG. 4.

According to a further particular aspect of the invention, the controller 9 may be adapted to convert the second images 6 to the .stl format and process the gray scale tones and/or the 3D spatial positions of the elements being imaged to transmit them to the display device 4 thereby affording real-time handling thereof by the healthcare professional D.

Thus, the healthcare professional D may manually adjust the gray scale tone values and the opacity of the second images 6 relative to the first images 3, as needed, to identify the objects to be represented on the display device 4, such as the soft or bone tissues, according to the density of the elements being imaged.

Advantageously, the system 1 may comprise a plurality of third images 13 adapted to represent, for example, virtual incisions and/or sutures, images of anchor or implant devices or surgery that may be done by a healthcare professional D on the anatomical site C.

Figure 5:
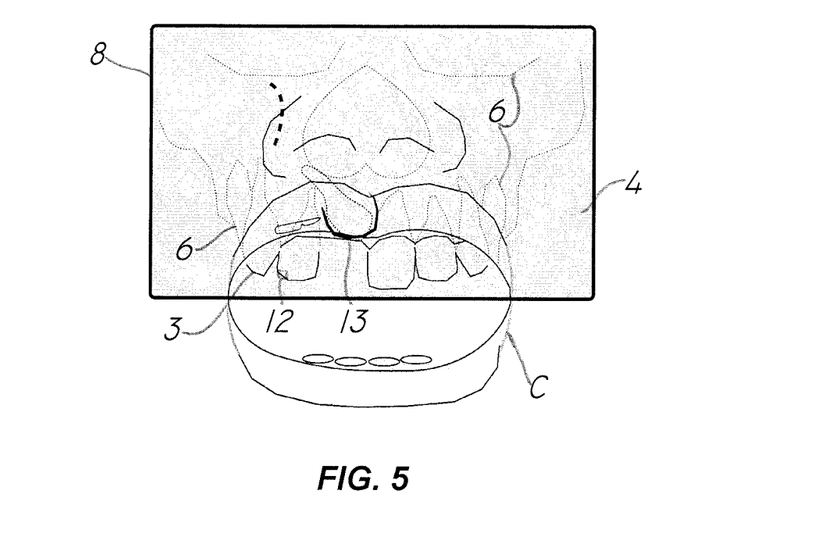
Figure 6:
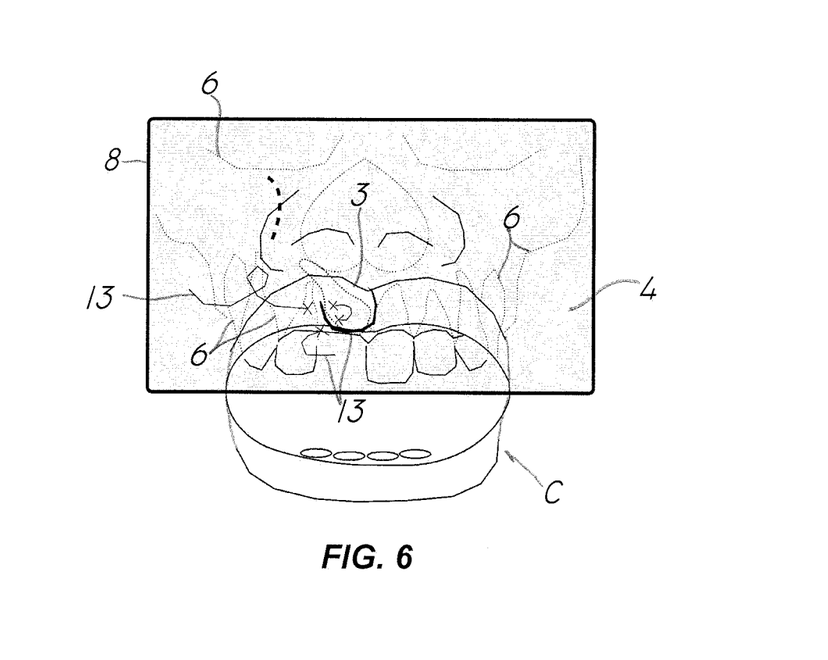

As shown in FIGS. 5 and 6, the third images 13 may be composed of dots, lines, and/or surfaces, which are transferred on the first 3 and/or the second images 6 automatically by artificial intelligence algorithms or manually by the healthcare professional D, and digitally entered into the storage means 7.

This additional advantage allows the healthcare professional D to simulate a surgical procedure and record the various steps thereof into the third images 13 during diagnosis, and later display them on the display device 4 via the controller 9 during inter-surgery.

By way of example and without limitation, the third images 13 can assist the healthcare professional D to represent the installation perimeter for anchor devices, such as implants, clamps, bolts, miniscrews, brackets, connectors and clips, on the first images 3 or the removal of tumor tissues on the second images 6, thereby avoiding the need of modeling the anatomical site C by dental records and transferring such information to the anatomical site C.

In a second embodiment of the invention, not shown, the system 1 may comprise video recording devices for real-time video recording of the augmented reality image 11 and means for detecting the vital values of the anatomical site C.

In this embodiment, the controller 9 may superimpose the vital data to the augmented reality image 11 and/or connect the electronic device 8 to an external videoconferencing or supervision system.

Thus, the electronic device 8 may connect to other devices of the same type and/or external computer-controlled devices to receive and/or transmit instructions, notifications and/or third additional images 13 by other clinical operators D or take interactive educational or experimental classes.

As is known, if the images 3, 6, 11, 13 or the vital data are recorded and/or shared, during both diagnosis and inter-surgery, patient information may be suitably encrypted for privacy protection.

Furthermore, the electronic device 8 may be able to connect to the external server 10 to upload the first 3, second 6 and third 13 images and automatically convert the second images 6.

Advantageously, the electronic device 8 may be connected via wireless means to electronic instruments used by the healthcare professional D, which may include position sensors adapted to transmit alarm signals to the electronic device 8 in the case of proximity with critical vascular or nervous structures or other internal structures in the anatomical site C, which are highlighted automatically by the controller 9 or manually by the healthcare professional D in the second 6 or third images 13.

In an alternative embodiment, not shown, the system 1 may comprise support means allowing the electronic device 8 to be placed between a healthcare professional D and the site C.

These support means may be of a type that may be worn by the healthcare professional D, placed on a stable surface or secured to the patient to reduce his movements.

Furthermore, the electronic device 8 may be held in a hand of the healthcare professional D or his assistant and be of a type that can be sterilized for surgical use.

According to a further aspect, the invention relates to a method of augmented reality imaging of an anatomical site C using a system as described above.

The method of the invention includes a first step of a) capturing at least one second anatomical image 6 and storing it in the storage means 7 in a standard .dcm format.

Furthermore, an additional step is provided for creating the third images 13, which are designed to simulate incisions and/or sutures, images of anchor devices or surgery that may be done by the healthcare professional D on the anatomical site C which are transferred to the first images 3 and/or second images 6 and store them in the storage means 7.

Figure 1:
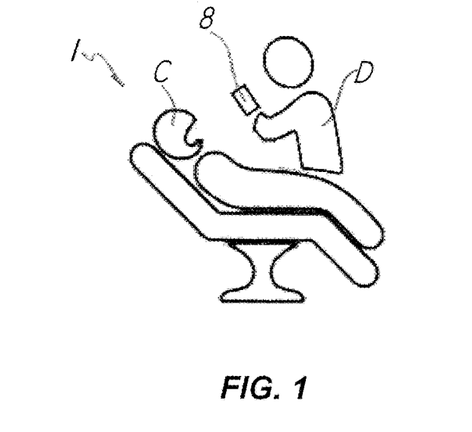
FIGS. 1 and 2 are schematic views of the system for augmented reality imaging of an anatomical site of the invention.

The method also includes a step of b) providing an electronic device 8 and placing it between the healthcare professional D and the anatomical site C and a step of c) actuating the electronic device 8 for capturing the first real-time images 3 of the anatomical site C, as shown in FIG. 1.

A step is provided of d) actuating the controller 9 to convert the second images to the .stl format and anchor the second images 6 to the first images 3 via the reference elements 12 to generate the augmented reality image 11.

As shown in FIGS. 3A to 4, a step is further provided of e) displaying the augmented reality image 11 in the display device 4 and handling the second images 6 by the healthcare professional D according to the gray scale tones corresponding to the density of the elements being displayed in accordance with a Hounsfield unit scale and/or a 3D spatial position and possibly resizing the second images 6.

Furthermore, a step is provided of f) creating a plurality of third images 13, which are designed to simulate incisions and/or sutures, images of anchor devices or surgery that may be carried out by the healthcare professional D on the anatomical site C which are transferred on the first 3 and/or second 6 images and store them into the storage means 7.

In addition, as best shown in FIGS. 5 and 6, the third images 13 are superimposed on the augmented reality image 11 to assist surgery that is designed to be done by a healthcare professional D on the anatomical site C.

Preferably, the method of augmented reality imaging of an anatomical site C using the system 1 may be used in the field of general surgery, bone surgery, intracranial surgery, neurosurgery, vascular microsurgery, orthodontics, dental surgery, diagnosis and/or dentistry.

The system 1 of the invention has been tested in the field of dentistry on an anatomical site C constituted by the stomatognathic system of a patient suffering from dental inclusion in bone tissue with overlapping roots of adjacent tooth elements and complications caused by the proximity of adjacent structures as shown in FIGS. 5 to 8.

The test was conducted using a system 1 having the following characteristics:

an electronic device 8 consisting of a smartphone iPhone 6 with an operating system iOS 10.2.1, whose stability was ensured by a support anchored to the ground and positioned between the healthcare professional D and the patient, a display device 4 consisting of a touchscreen with a screen size of 375×667 points and an aspect ratio of 3×, a capture device 2 consisting of an 8 MP camera, a controller 9 consisting of a 64 bit Apple A8 processor and an application developed with a SWIFT+C language by ARkit, Ulkit and metal, first images 3 of the mouth of the patient sitting at 90° in the dental chair and with the head of the patient in the N.H.P. (Natural Head Position), second 6 images consisting of a file with a .dcm extension representing the upper arch of the anatomical site C and obtained through cone beam X ray catalyst with voxel units containing information about the 3D spatial position of the elements and a Hounsfield scale with a range set to values between −1350Hu and 1650Hu, reference elements 12 consisting of the profile of a central incisor and a lateral incisor of the upper arch, third images 13 consisting of a file having a .dwg extension representing virtual incision lines and the positioning of a connector for orthodontic extrusion with light forces exactly at the center of the crown.

The test resulted in easier interpretation of diagnostic images by the healthcare professional and enhanced perception of treatment effectiveness by the patient, as well as in reduced overall surgery times.

Figure 7:
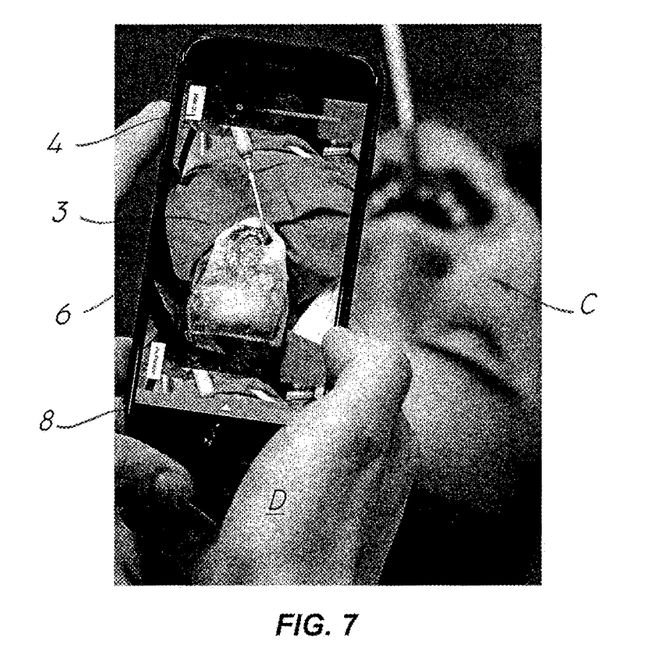
FIG. 7 is an example of the system of FIG. 2 for imaging an anatomical site.
Figure 8A:
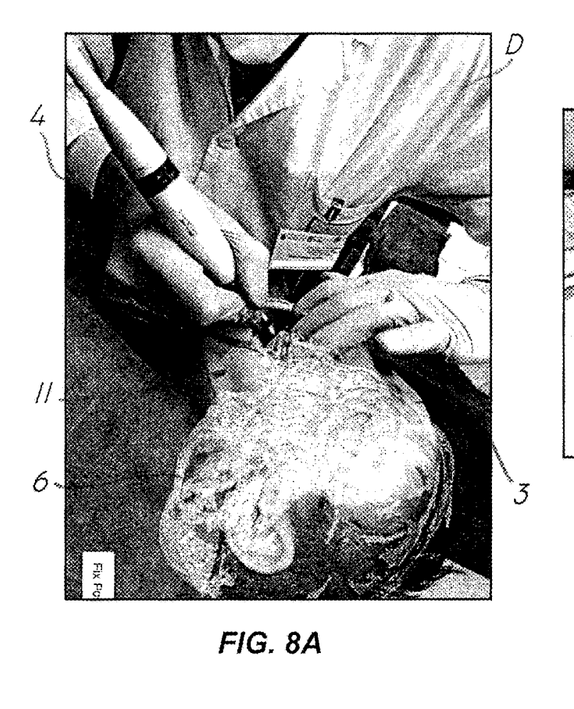
FIGS. 8A and 8B are examples of imaging of an anatomical site using the system of FIG. 2.
Figure 8B:
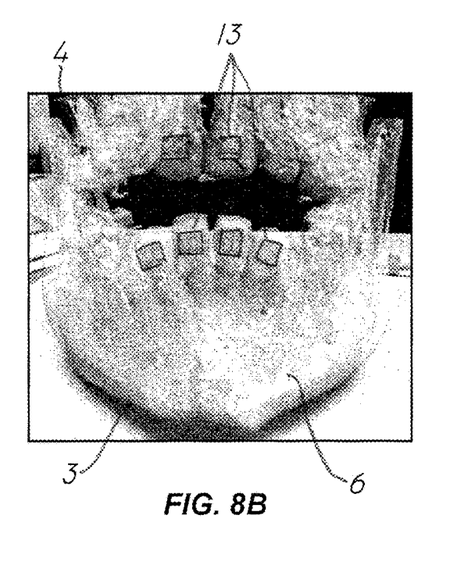

For example, as best shown in FIGS. 7 and 8, the augmented reality image 11 appearing on the display device 4 is apparently found to be clipped to the anatomical site C via the common reference elements 12, irrespective of the spatial position of the electronic device 8 as the latter is being moved relative to the anatomical site C.

It will be appreciated from the foregoing that the system and the method for Augmented Reality imaging of an anatomical site fulfill the intended objects, and can particularly assist the healthcare professional during surgery, irrespective of the position of the anatomical site.

While the system has been described with particular reference to the accompanying figures, the numerals referred to in the disclosure and claims are only used for the sake of a better intelligibility of the invention and shall not be intended to limit the claimed scope in any manner.

Reference herein to "one embodiment" or "the embodiment" or "some embodiments" indicates that a particular characteristic, structure or element that is being described is included in at least one embodiment of the inventive subject matter.

Furthermore, the particular characteristics, structures or elements may be combined together in any suitable manner to provide one or more embodiments.

INDUSTRIAL APPLICABILITY

The present invention can find application in industry as it can be produced on an industrial scale in the field of dentistry and controller-assisted medicine, namely in the field of orthodontics, dental surgery and/or diagnosis.

The invention claimed is:

1. A system (1) for dynamic augmented reality imaging of an anatomical site (C) in the field of orthodontics, dental surgery, or dentistry, comprising:
    at least one image capturing device (2) for capturing first real-time 3D images (3) of the anatomical site (C);
    at least one display device (4) for real-time display of said first 3D images (3) captured by said capture device (2);
    storage means (7) for storing at least one second 3D anatomical image (6) of the site (C);
    an electronic device (8) comprising a controller (9) configured to receive and process said first 3D images (3) and said second 3D images (6);
    wherein said controller (9) is configured to display on said display device (4) an augmented reality image (11) obtained by superimposing said second 3D image (6) on said first 3D image (3) while identifying common reference elements (12) of said first 3D image (3) and of said second 3D image (6);
    wherein said common reference elements (12) are anthropometric or cephalometric points or relevant points of craniofacial structures and are identified automatically by said controller (9) or manually by a healthcare professional (D);
    and wherein said second image (6) is a non-virtual 3D image that is obtained from portions of fan beam or cone beam computed tomography (CBCT) or magnetic resonance images showing internal structures of the anatomical site (C) that are invisible to the naked eye that depict critical structures of vascular, nervous, lymphatic or complex radical systems, said augmented reality image (11) being clipped to the anatomical site (C) by means of said common reference elements (12), irrespective of the spatial position of said electronic device (8) during displacements of the electronic device (8) relative to the anatomical site (C), wherein said augmented reality image (11) is a dynamic 3D image that moves relative to any movements of the anatomical site or any movements of the electronic device (8).

2. A system (1) for dynamic augmented reality imaging of an anatomical site (C) in the field of orthodontics, dental surgery, or dentistry, comprising:
    at least one image capturing device (2) for capturing first real-time 3D images (3) of the anatomical site (C);
    at least one display device (4) for real-time display of said first 3D images (3) captured by said capture device (2);
    storage means (7) for storing at least one second 3D anatomical image (6) of the site (C);
    an electronic device (8) comprising a controller (9) configured to receive and process said first 3D images (3) and said second 3D images (6);
    wherein said controller (9) is configured to display on said display device (4) an augmented reality image (11) obtained by superimposing said second 3D image (6) on said first 3D image (3) while identifying common reference elements (12) of said first 3D image (3) and of said second 3D image (6);
    wherein said common reference elements (12) are anthropometric or cephalometric points or relevant points of craniofacial structures and are identified automatically by said controller (9) or manually by a healthcare professional (D); and wherein said second image (6) is a non-virtual 3D image that is obtained from portions of fan beam or cone beam computed tomography (CBCT) or magnetic resonance images showing internal structures of the anatomical site (C) that are invisible to the naked eye that depict critical structures of vascular, nervous, lymphatic or complex radical systems, said augmented reality image (11) being clipped to the anatomical site (C) by means of said common reference elements (12), irrespective of the spatial position of said electronic device (8) during displacements of the electronic device (8) relative to the anatomical site (C), further comprising a plurality of third images (13) of virtual incisions and/or sutures, images of anchor or implant devices or surgery that may be done by a healthcare professional (D) on the anatomical site (C), said third images (13) being composed of dots, lines and/or surfaces, which are transferred onto said first images (3) and/or second images (6) automatically, using artificial intelligence algorithms or manually by the healthcare professional (D), and are digitally loaded into said storage means (7), wherein said augmented reality image (11) is a dynamic 3D image that moves relative to any movements of the anatomical site (C) or any movements of the electronic device (8).

3. The system as claimed in claim 2 wherein said electronic device (8) is connected wirelessly to electronic instruments, used by the healthcare professional (D), which comprise position sensors adapted to transmit alarm signals to said electronic device (8) when in proximity to critical vascular or nervous structures or other internal structures in the anatomical site (C), which are displayed automatically by said controller (9) or manually by the healthcare professional (D) in said second images (6) or third images (13).

4. The system as claimed in claim 1, wherein said second images (6) are stored as .dcm or .stl formats in said storage means (7) and have gray scale tones corresponding to the density of the elements being imaged as Hounsfield units and/or a 3D spatial position.

5. The system as claimed in claim 1, wherein said controller (9) is adapted to convert said second images (6) to the .stl format and to process said gray scale tones and/or 3D spatial positions to transmit the gray scale tones and/or 3D spatial positions to said display device (4) for real-time handling thereof using artificial intelligence algorithms or by the healthcare professional (D).

6. A system (1) for dynamic augmented reality imaging of an anatomical site (C), in the field of orthodontics, dental surgery, or dentistry comprising:

an electronic device (8), configured as a smartphone or tablet, comprising:
  at least one image capturing device (2) for capturing first real-time 3D images (3) of the anatomical site (C);
  at least one display device (4) for real-time display of said first 3D images (3) captured by said capture device (2);
  storage means (7) for storing at least one second anatomical 3D image (6) of the site (C); and
  a controller (9) configured to receive and process said first 3D images (3) and said second 3D images (6);
  wherein said controller (9) is configured to display on said display device (4) an augmented reality image (11) obtained by superimposing said second 3D image (6) on said first 3D image (3) while identifying common reference elements (12) of said first 3D image (3) and of said second 3D image (6);
  wherein said common reference elements (12) are anthropometric or cephalometric points or relevant points of craniofacial structures and are identified automatically by said controller (9) or manually by a healthcare professional (D);
  and wherein said second image (6) is a non-virtual 3D image that is obtained from portions of fan beam or cone beam computed tomography (CBCT) or magnetic resonance images showing internal structures of the anatomical site (C) that are invisible to the naked eye that depict critical structures of vascular, nervous, lymphatic or complex radical systems, said augmented reality image (11) being clipped to the anatomical site (C) by means of said common reference elements (12), irrespective of the spatial position of said electronic device (8) during displacements of the electronic device (8) relative to the anatomical site (C), wherein said augmented reality image (11) is a dynamic 3D image that moves relative to any movements of the anatomical site (C) or any movements of the electronic device (8) and, wherein said electronic device (8) further comprises an accelerometer and a gyroscope.

7. The system as claimed in claim 1, wherein said electronic device (8) is a smartphone or a tablet, said capture device (2) being a camera and said display device (4) being a touchscreen of said electronic device (8).

8. The system as claimed in claim 1, wherein said storage means (7) are incorporated in said electronic device (8) or an external server (10), said electronic device (8) being adapted to be connected by means of wireless connections to said server (10).

9. The system as claimed in claim 1, further comprising recording devices for real-time recording of said augmented reality image (11) and means for detecting the vital data of the anatomical site (C), said controller (9) being adapted to superimpose said data onto said augmented reality image (11) and/or to connect said electronic device (8) to an external videoconferencing or supervision system.

10. The system as claimed in claim 1, further comprising support means adapted to position said electronic device (1) between the healthcare professional (D) and the anatomical site (C), said support means being adapted to be worn by the healthcare professional (D) or laid on a stable surface.

11. The system as claimed in claim 1, wherein the anatomical site (C) comprises the stomatognathic system and said common reference elements (12) correspond to elements of the image of the dental structure or other anatomical reports.

12. A method of dynamic augmented reality imaging of an anatomical site (C) using a system (1) as claimed in claim 1, the method comprising:
  a) capturing said at least one second anatomical image (6) and storing it in said storage means (7), said second image (6) being stored in a .dcm format;
  b) providing said electronic device (8) and placing it between the healthcare professional (D) and the anatomical site (C);
  c) actuating said electronic device (8) for capturing said first real-time images (3) of the anatomical site (C);
  d) actuating said controller (9) to convert said second images (6) to the .stl format and anchor said second images (6) to said first images (3) via said common reference elements (12) to generate said augmented reality image (11);
  e) displaying said augmented reality image (11) in said display device (4) and handling said second images (6) by the healthcare professional (D) according to the gray scale tones corresponding to the density of the elements being imaged as Hounsfield units and/or a 3D spatial position and/or resizing the second images (6).

13. The method as claimed in claim 12, further comprising: f) creating a plurality of third images (13), which are adapted to simulate incisions and/or sutures, images of anchor devices or surgery that may be done by the healthcare professional (D) on the anatomical site (C) which are transferred to said first images (3) and/or said second images (6) and store them in said storage means (7).

14. The method as claimed in claim 13, wherein said third images (13) are superimposed on said augmented reality image (11) to assist surgery that is designed to be done by a healthcare professional (D) on the anatomical site (C).

15. A use of the method of augmented reality imaging of an anatomical site (C) as claimed in claim 12 in a field selected from the group consisting of: general surgery, bone surgery, intracranial surgery, neurosurgery, vascular microsurgery, orthodontics, dental surgery, diagnosis and dentistry.

* * * * *